(12) United States Patent
Fries et al.

(10) Patent No.: US 7,879,622 B1
(45) Date of Patent: Feb. 1, 2011

(54) BARRIER-PERMEABLE PROXY REPORTER ANALYSIS

(75) Inventors: David Fries, St. Petersburg, FL (US); Brian Gregson, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 707 days.

(21) Appl. No.: 11/837,919

(22) Filed: Aug. 13, 2007

Related U.S. Application Data

(60) Provisional application No. 60/822,143, filed on Aug. 11, 2006.

(51) Int. Cl.
 *G01N 33/566* (2006.01)
(52) U.S. Cl. ...................................... 436/501
(58) Field of Classification Search .................. 436/501
 See application file for complete search history.

(56) References Cited

U.S. PATENT DOCUMENTS

| | | | |
|---|---|---|---|
| 6,750,031 B1 * | 6/2004 | Ligler et al. | 435/7.93 |
| 6,974,704 B2 * | 12/2005 | Nelson et al. | 436/173 |
| 2005/0048553 A1 * | 3/2005 | Chenna et al. | 435/6 |
| 2005/0155861 A1 * | 7/2005 | Guzman | 204/451 |
| 2009/0088982 A1 * | 4/2009 | Fukushima et al. | 702/23 |

FOREIGN PATENT DOCUMENTS

| | | |
|---|---|---|
| WO | WO2005037210 A2 | 4/2005 |
| WO | WO2005037210 A3 | 4/2005 |

OTHER PUBLICATIONS

Thomas Briese, Diagnostic System for Rapid and Sensitive Differential Detection of Pathogens,(Journal: Emerging Infectious Diseases),Feb. 2005, 310-313, 11(2).

Patricia Bottari, Design and Synthesis of Visible Isotope Coded Affinity Tags for the Absolute Quantification of Specific Proteins in Complex Mixtures, (Bioconjugate Chem), 2004, pp. 380-388, vol. 15 No. 2.

* cited by examiner

*Primary Examiner*—Melanie Yu
*Assistant Examiner*—Gary W Counts
(74) *Attorney, Agent, or Firm*—Smith & Hopen, P.A.

(57) ABSTRACT

Analysis of complex media (e.g.—blood and seawater) is difficult because the media are composed of particles of different sizes and chemical profiles. Disclosed is a method for the detection of a constituent in a medium that enhances the molecular selectivity of a detector by separating the detector from the medium by a membrane of specified permeability. Proxy reporters are employed to enhance particle specificity. The novel combination of the invention has application to chemical detection in a broad range of fields.

9 Claims, 10 Drawing Sheets

BARRIER-PERMEABLE PROXY REPORTER ANALYSIS

CROSS-REFERENCE TO RELATED DISCLOSURES

This application claims priority to a provisional application filed Aug. 11, 2006, bearing application No. 60/822,143.

FIELD OF INVENTION

This invention relates to analytical detection of molecules within a sample, and more specifically, to a novel analysis system that quantifies the presence of a molecule by proxy.

BACKGROUND OF THE INVENTION

A complex medium is a system that has a large number of distinct chemical components. Particles in a complex medium vary widely in size and chemical profile. These media do not readily lend themselves to chemical analysis of specific constituent of group of constituents because the components of a complex medium are frequently difficult to separate. Examples of complex media include blood, seawater and crude petroleum.

There is a need for an efficient method of assaying a sample of a complex medium to determine the presence of a particular constituent. Efficient assaying of complex media will enhance chemical detection across a broad range of fields. For example, the medical practitioner will assess the presence of toxins in blood or sera with greater accuracy and specificity. The environmental practitioner will assess the presence of pollutants in a body of water with greater speed and resolution.

The present invention is a method that adds a tag to a constituent particle, separates the tag from the particle, passes the tag through a membrane, and then analyzes the collection of tags. The invention is distinct from the prior art as it passes tags through a membrane designed to accommodate the measurement of particles of disparate sizes and chemical profiles. The invention offers greater selectivity than the prior art because it allows the researcher to more narrowly focus molecular recognition by manipulating the membrane permeability and mass selectivity A tag is an identifying marker that can be attached to and removed from a molecule without permanently altering the molecule. Tags are used to help identify a target molecule because it may be easier to detect and manipulate the tags than to detect and manipulate the target particle itself.

A membrane is a barrier that separates two phases and delineates the molecules that can pass between the two phases. The use of a membrane may conserve resources that the researcher would have expended using conventional methods of separation, e.g., distillation. Membrane structures vary according to the nature of the reactants and the properties of the molecules that are selected to pass between phases. Membranes may be homogenous or heterogenous, symmetric or asymmetric and solid or liquid. The researcher can charge the membrane, render it bipolar or neutral. Method of transport varies as well. The researcher can select a membrane that uses a charge, temperature or pressure gradient.

A detector is any apparatus capable of registering and/or quantifying the presence of a target.

SUMMARY OF INVENTION

An embodiment of the invention includes the steps of preselecting proxy reporters that bind to target molecules, introducing the reporters to a fluid sample, the reporters provided in a sufficient concentration to saturate all available target molecules, purifying the sample to remove excess reporters, unbinding the remaining reporters in the sample from their respective molecules, providing a membrane selectively permeable to the unbound reporters, migrating the unbound reporters across the membrane leaving the fluid sample substantially unaltered, and quantifying the unbound reporters that migrated across the membrane whereby the quantification correlates to the presence of target molecules in the sample.

The quantification may be performed by an analytical detector including, but not limited to optical detectors, electrochemical detectors and mass spectrometers. The unbinding step may be effectuated by any suitable method known in the art including photocleaving, chemical reaction, antibody recognition, molecular imprinted polymer reaction, oligonucleotide linkage and metal affinity reaction.

An alternative embodiment of the invention includes the steps of preselecting a first proxy reporter that binds to a first target molecule, preselecting a second proxy reporter that binds to a second target molecule, introducing the first and second proxy reporters to a fluid sample, the reporters provided in a sufficient concentrations to saturate all available target molecules, purifying the sample to remove excess reporters, unbinding the remaining reporters in the sample from their respective molecules, providing a membrane selectively permeable to the unbound reporters whereby the first proxy reporter migrates through the membrane at a first rate and the second proxy reporter migrates through the membrane at a second rate, migrating the unbound reporters across the membrane leaving the fluid sample substantially unaltered, and quantifying the unbound reporters that migrated across the membrane on a temporal basis whereby the quantification correlates unbound reporters migrating through the membrane at the first rate with the presence of the first target molecule in the sample and the unbound reporters migrating through the membrane at the second rate with the presence of the second target molecule in the sample. The first and second proxy reporters may be variable mass units, the first proxy reporter having a mass value quantitatively distinct from a mass value of the second proxy reporter.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
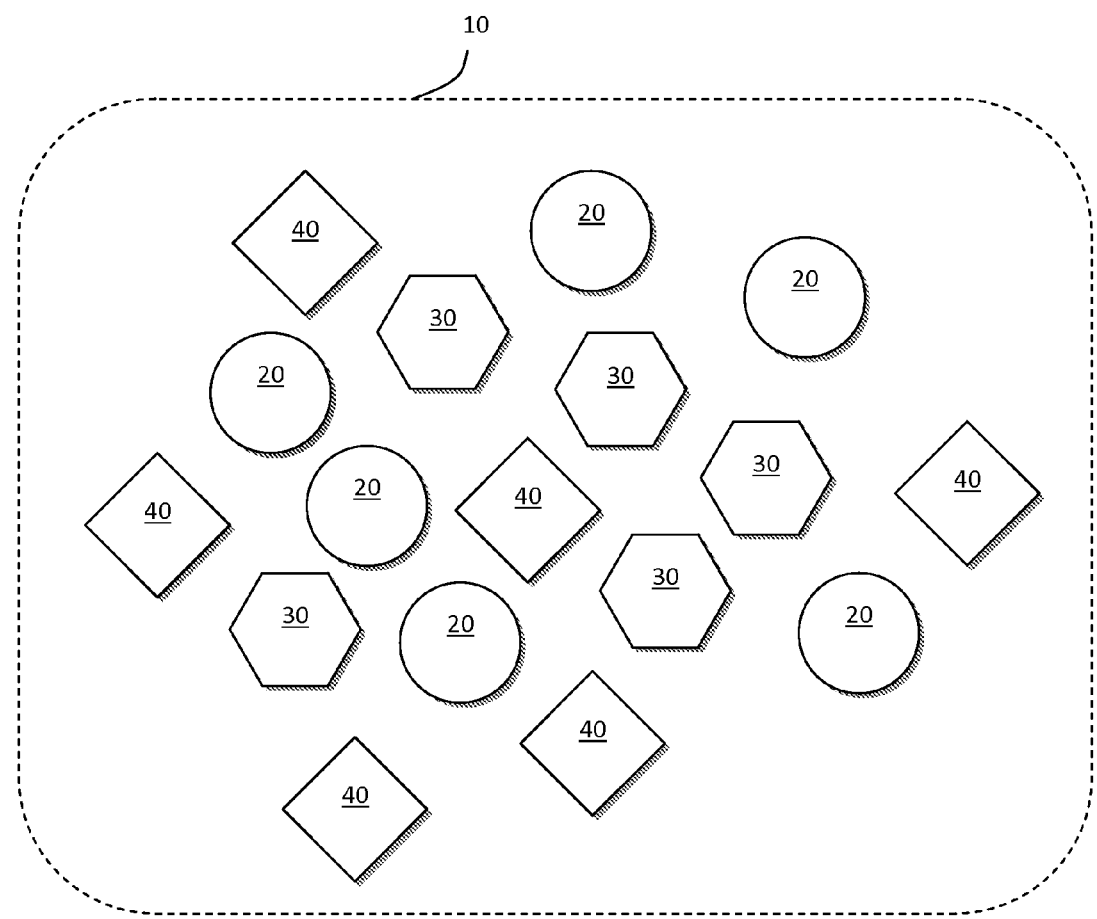
FIG. 1 is a diagrammatic view of a fluid sample containing three types of molecules.

The invention discloses a method for analyzing and detecting specified molecules using separable tags where the detector is separated from the sample by a barrier membrane that allows said tags to pass but prevents said sample molecules from passing. The invention discloses the attachment of a removable tag, probe, marker or other identifier to a molecular, chemical or cellular target. In a preferred embodiment, this tag is a variable mass unit tag. A variable mass unit tag is a tag that can be shaped to specification because the variable mass unit can be manipulated to alter the molecular weight of the tag. For example, a complex medium is composed of particles between 500 Daltons and 900 Daltons. The membrane chosen is permeable only to particles with less mass than 400 Daltons. A tag of about 350 Daltons will penetrate the membrane. The membrane is impermeable to the remaining molecules, including those of the target constituent. In an alternative embodiment, the tag is a proxy-reporter probe. In an alternative embodiment, the tag is a membrane transporter. In an alternative embodiment, the tag is a tag of low molecular weight. These embodiments are merely exemplary and are not intended to limit the scope of the claimed invention.

The invention discloses the attachment of a removable tag, probe, marker or other identifier to a molecular, chemical or cellular target. In a preferred embodiment, this tag is photocleavable or photolabile. The Masscode™ genotyping system developed by Quiagen is an exemplary system of attaching tags. In an alternative embodiment, the tag is attached and separated from the target molecule through a chemical reaction. In an alternative embodiment, the tag attaches to and separates from the target molecule using an antibody recognition mechanism. In an alternative embodiment, the tag attaches to and separates from the target molecule using a molecular imprinted polymer. In an alternative embodiment, the tag attaches to the target molecule using an oligonucleotide linkage. In an alternative embodiment, the tag attaches to and separates from the target molecule through metal affinity.

The invention discloses the use of a membrane to separate the detector from the complex medium. An appropriate membrane is selected based on parameters known to one skilled in the art. Membrane permeability is selected that is compatible with both the tags that are intended to pass through the membrane and the particles from the medium that are not intended to pass through the membrane. Material of the membrane is selected to be compatible with the medium under examination.

In an alternative embodiment, more than one target constituent is examined. Parameters known to those skilled in the art are used to determine a membrane configuration and tag mass that will allow for a temporal separation as well as a physical separation among the target constituents. Two molecular tags of different mass will pass through the membrane at different rates. The difference in the mass between the tags corresponds to the difference in the rate of passage across the membrane. The greater the mass, the slower the passage across the membrane.

The invention discloses the use of an analytical detector to ascertain details about a sample. In one embodiment, the detector is an optical detector. In another embodiment, the detector is an electrochemical detector. In a preferred embodiment the detector is a mass spectrometer.

Figure 2:
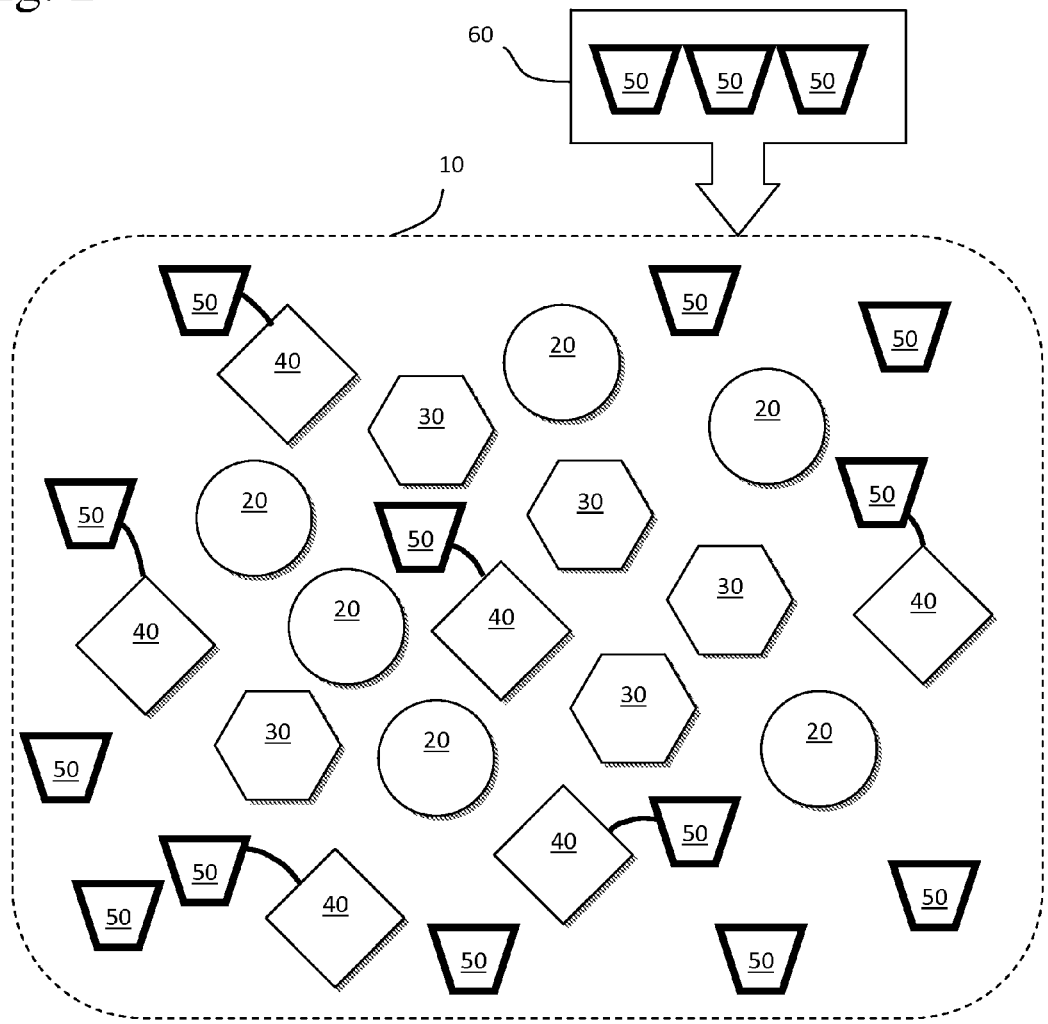
FIG. 2 is a diagrammatic view of proxy reporters introduced to the fluid sample and binding to their target molecule type.

Turning now to FIG. 1, first phase 10 is a fluid sample containing molecules 20, 30 and 40. Molecules 20-40 may include non-organic and/or organic matter such as cellular structures or cells themselves. In FIG. 2, proxy reporter 50 is introduced 60 into first phase 10. It can be seen that proxy reporter 50 only binds to molecule 40 and that a sufficient quantity of proxy reporter 50 is provided to the fluid sample to saturate all possible target molecules. Accordingly, the fluid sample would necessarily have at least some excess and unbound proxy reporter 50.

Figure 3:
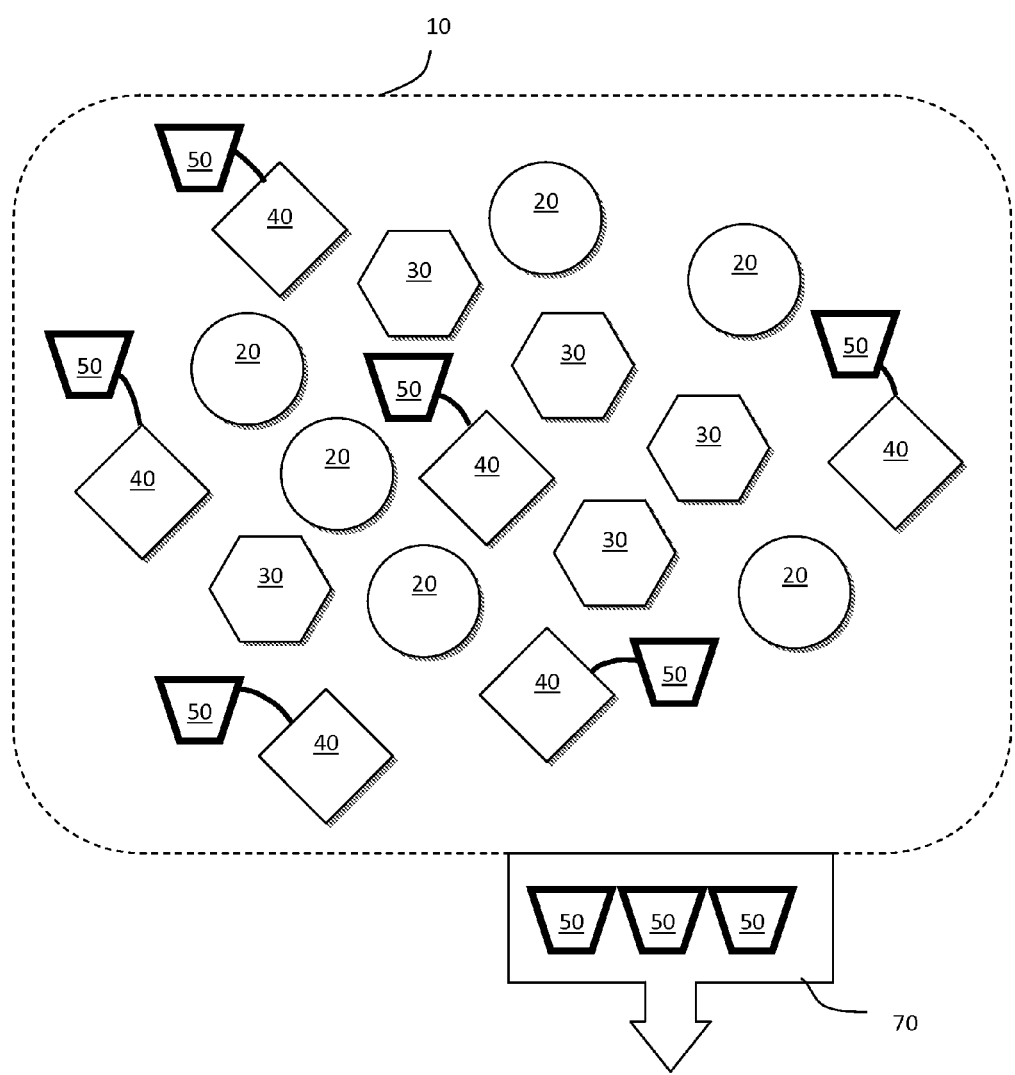
FIG. 3 is a diagrammatic view of a fluid sample purified to remove excess reporters.
Figure 4:
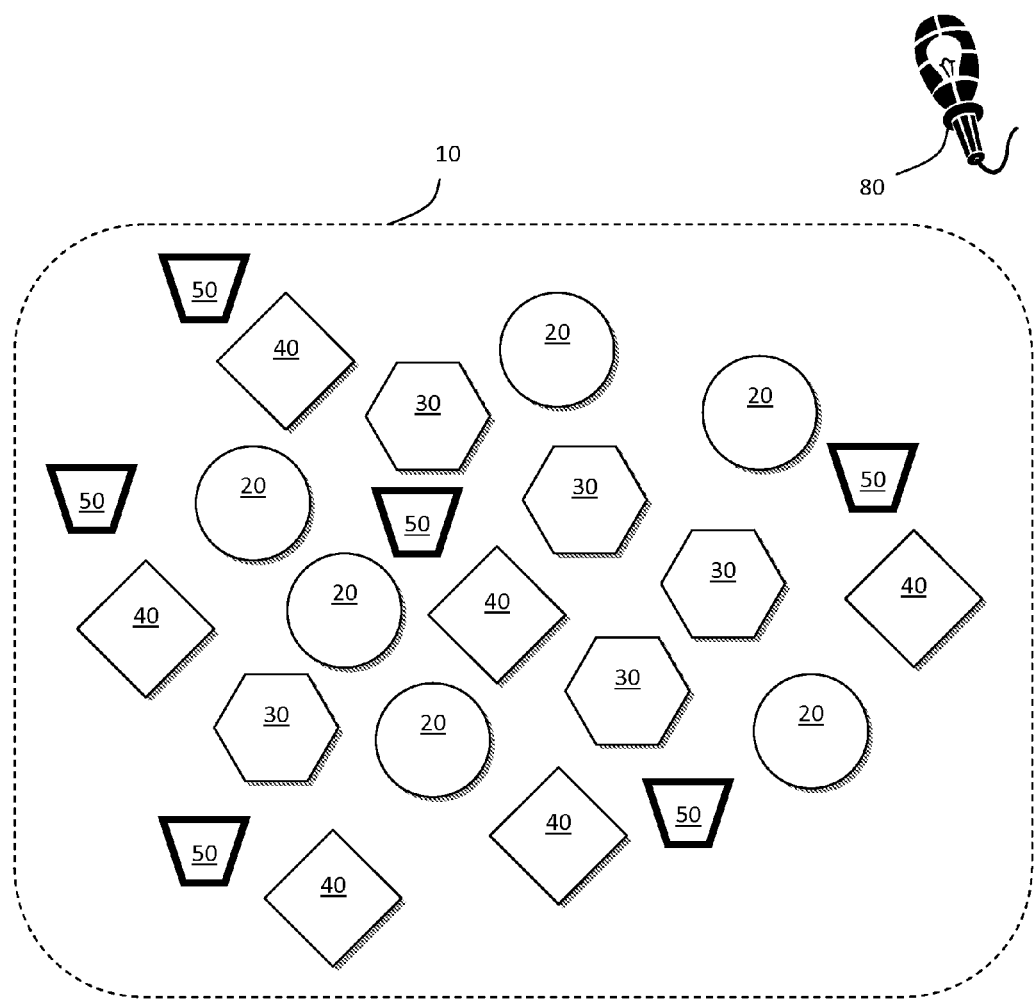
FIG. 4 is a diagrammatic view of a fluid sample exposed to light to photocleave the reporters from the target molecules.
Figure 5:
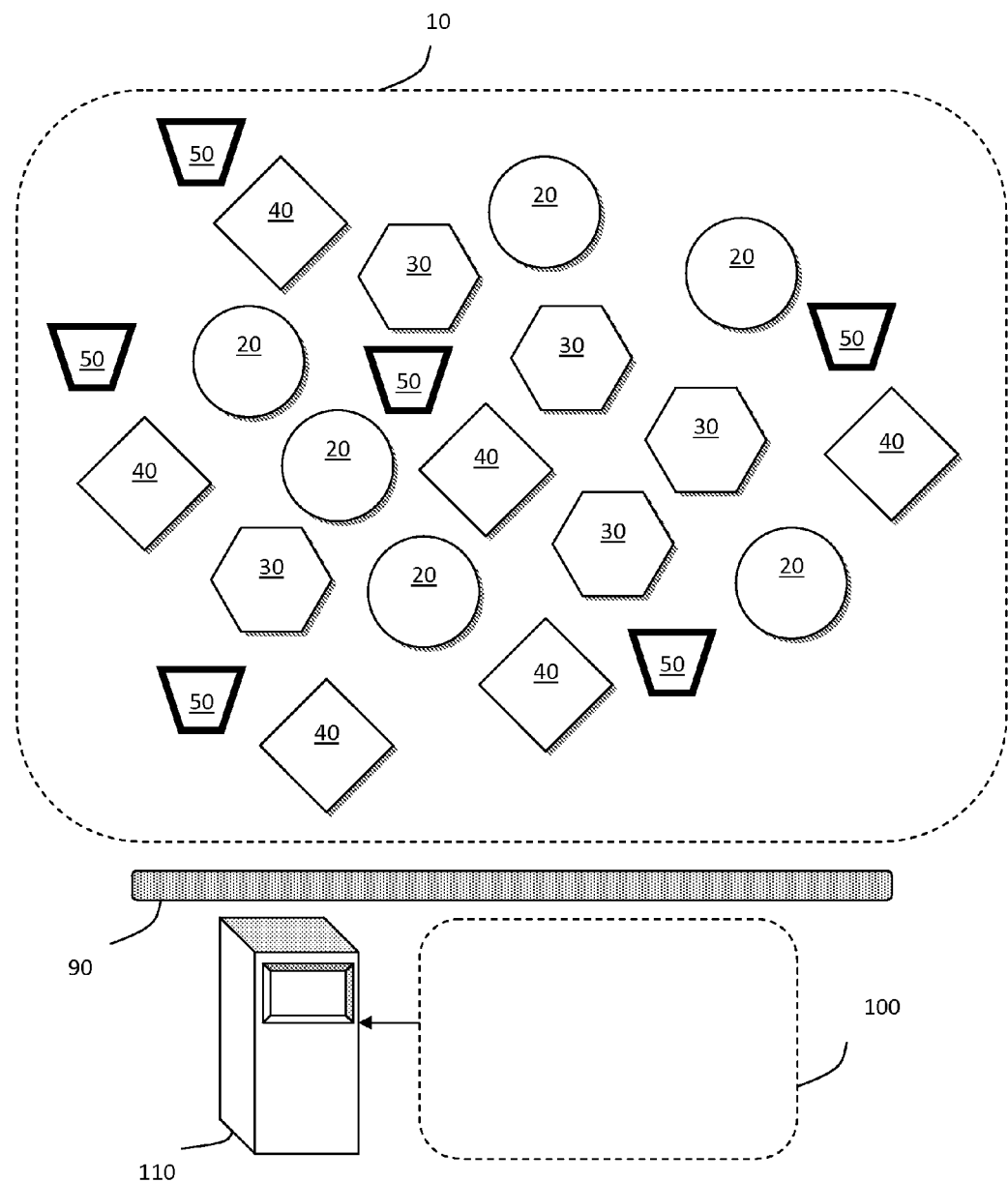
FIG. 5 is a diagrammatic view of a fluid sample in a first phase separated by a selectively permeable membrane from a second phase.

In FIG. 3, excess and unbound proxy reporter 50 is removed 70 from fluid sample whereby a one-to-one relationship remains between bound proxy reporter 50 and molecule 40. In FIG. 4, light 80 photocleaves proxy reporter 50 from molecule 40. The fluid sample still maintains a one-to-one relationship between (now) unbound proxy reporter 50 and molecule 40. In FIG. 5, first phase 10 is separated from second phase 100 by selectively permeable membrane 90. In the current exemplary embodiment, selectively permeable membrane 90 permits the migration of proxy reporter 50 but does not permit molecules 20-40 to pass. Coupled to second phase 100 is analytical detector 110.

Figure 6:
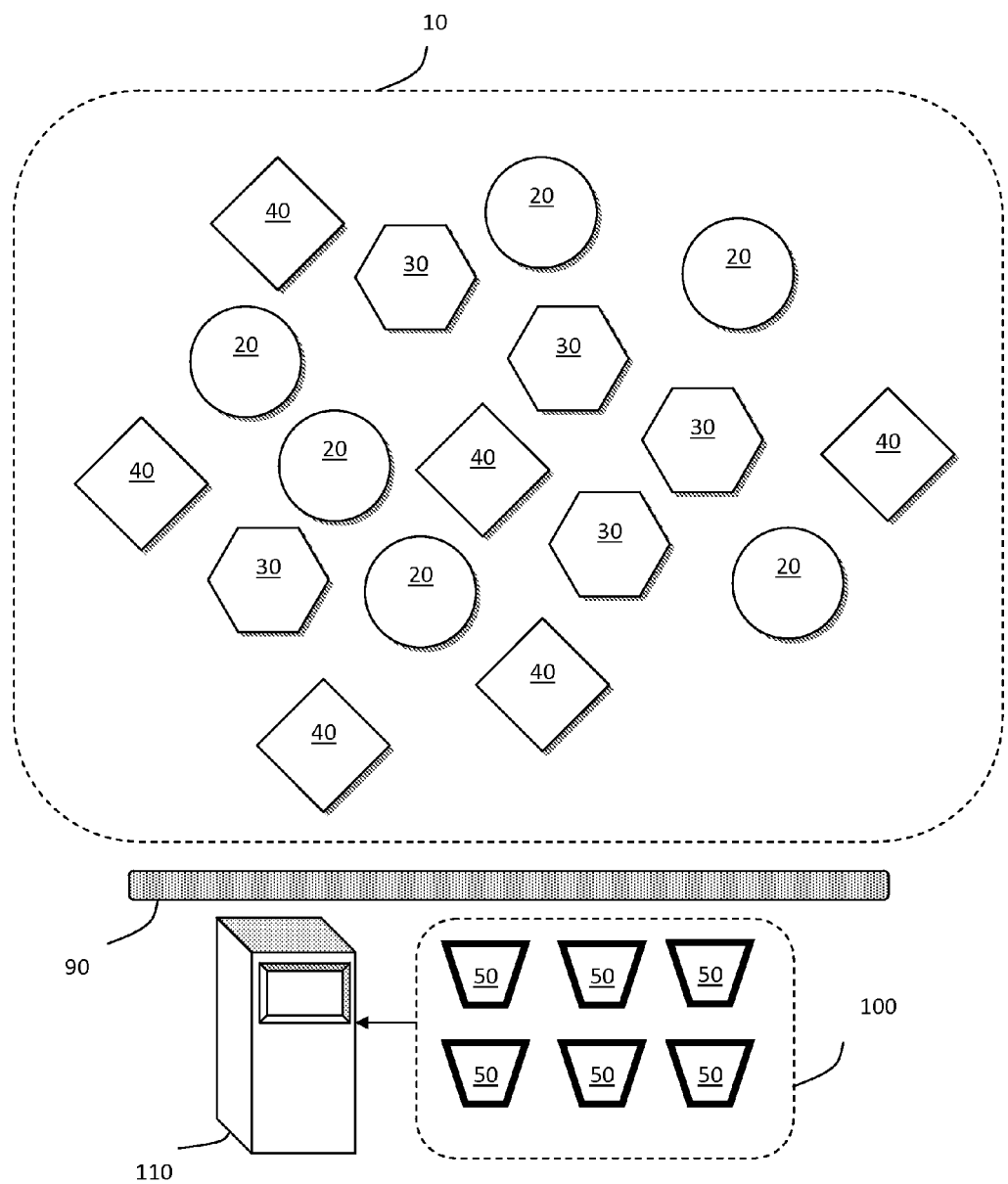
FIG. 6 is a diagrammatic view of a fluid sample showing the migration of unbound reporters across the membrane from the first phase to the second phase.

In FIG. 6, proxy reporters 50 have migrated from first phase 10, across selectively permeable membrane 90, to second phase 100. It should be noted that the fluid sample in first phase 10 is substantially unaltered from its original state. Proxy reporters 50 are quantified by analytical detector 110 which directly correlates to the quantity of molecule 40 in the fluid sample. The ability to quantify the presence and/or concentration of a molecule in a fluid sample without substantially altering the original fluid sample has significant utility for a large number of diagnostic, detection and monitoring applications.

Figure 7:
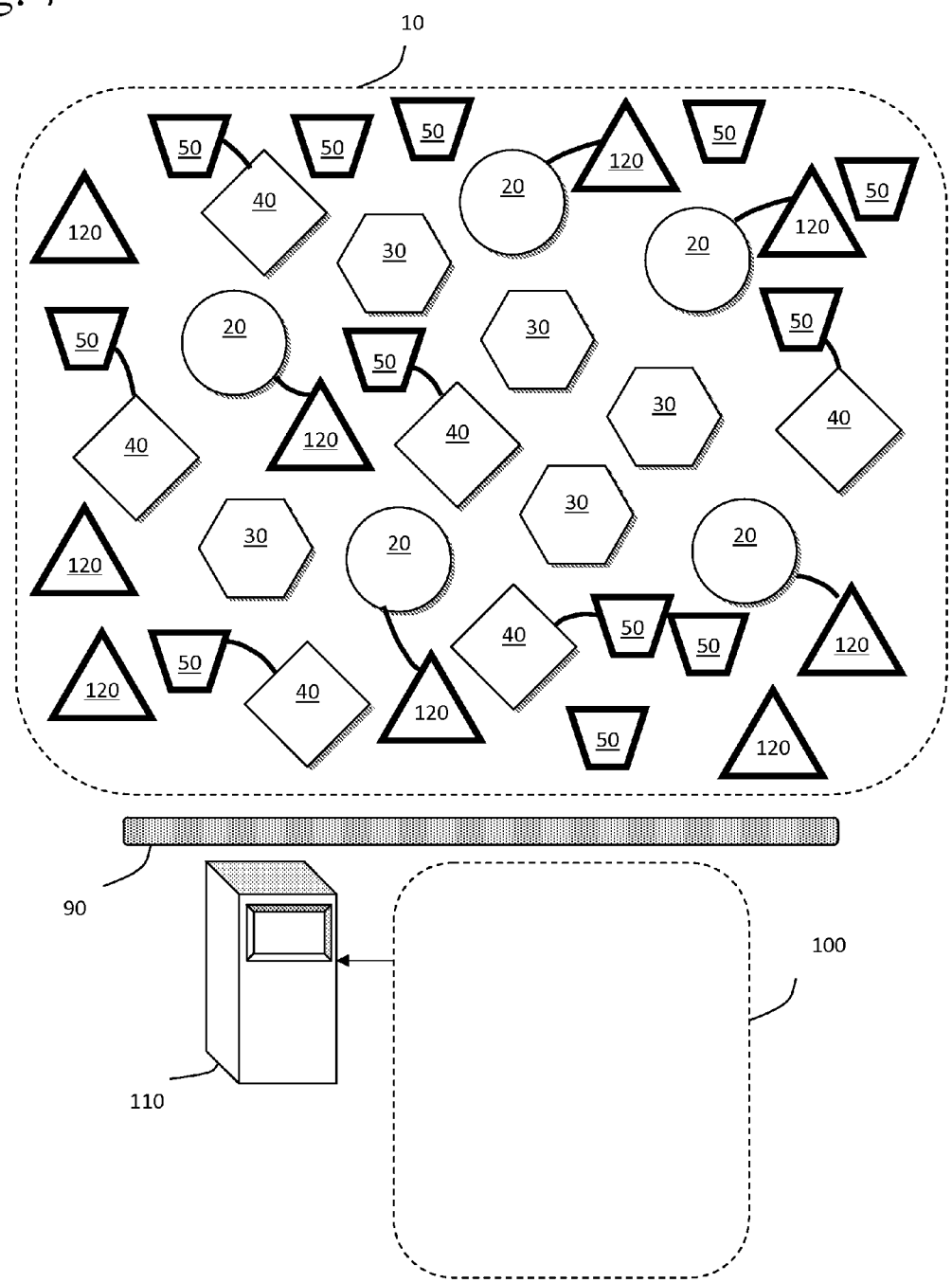
FIG. 7 is a diagrammatic view of a fluid sample wherein two types of proxy reporters bind to their respective target molecules and excess proxy reporters remain in the sample unbound.

In FIG. 7, first proxy reporter 50 binds to molecule 40 as previously illustrated in FIGS. 2-3. In addition, second proxy reporter 120 binds to molecule 120. In an embodiment of the invention, first proxy reporter 50 and second proxy reporter 120 have differing masses. Similar to that shown in FIG. 2, FIG. 7 shows excess proxy reporters that are unbound to their respective target molecules. This insures that the one-to-one correlation between proxy reporter and target molecule constitutes an accurate assumption.

Figure 8:
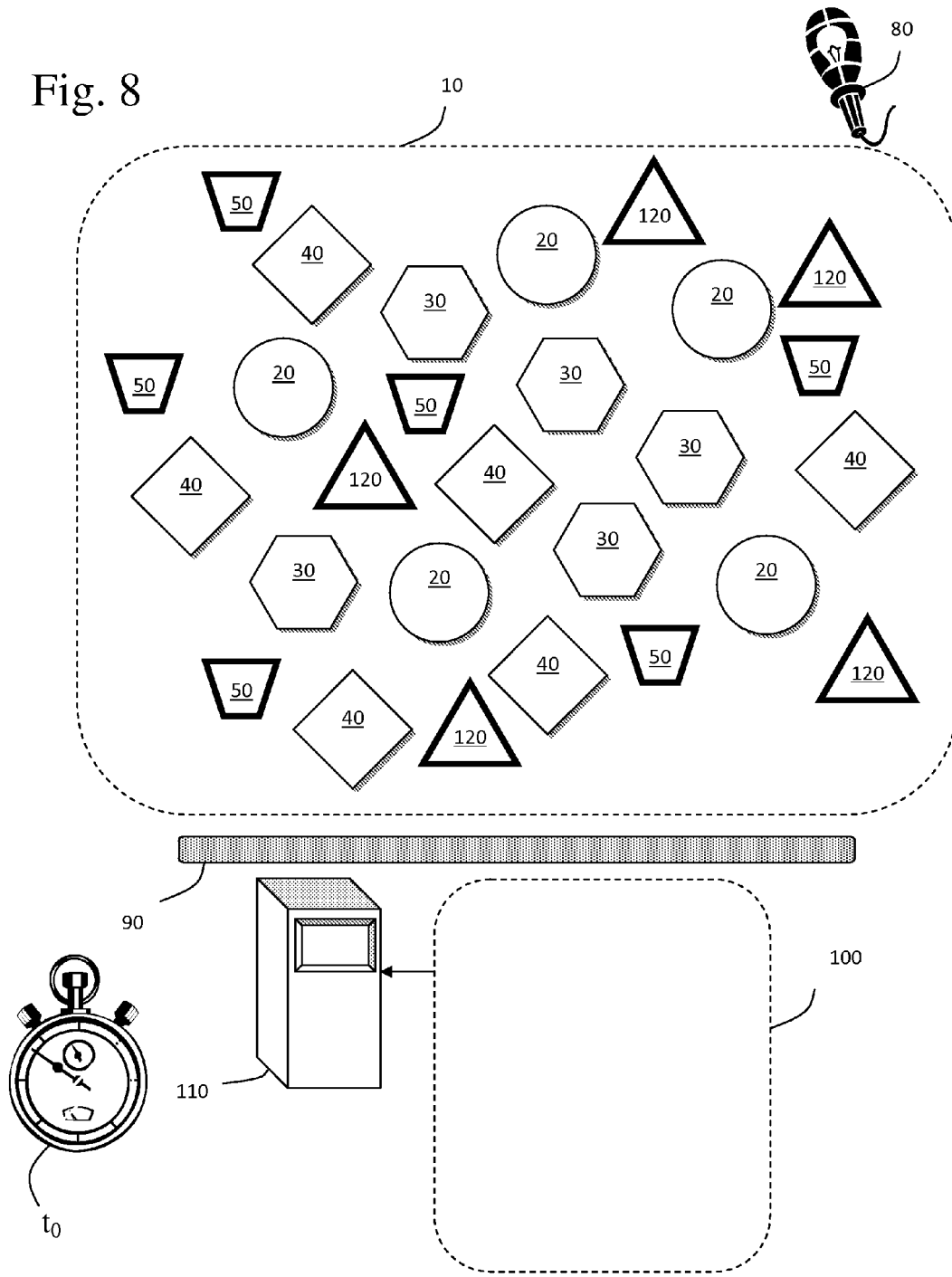
FIG. 8 is a diagrammatic view of a fluid sample exposed to light to photocleave the bound proxy reporters from their respective target molecules.

In FIG. 8, excess and unbound first proxy reporter 50 and second proxy reporter 120 have already been removed from the fluid sample. Light 80 photocleaves first proxy reporter 80 from molecule 40 and second proxy reporter 120 from molecule 20.

Figure 9:
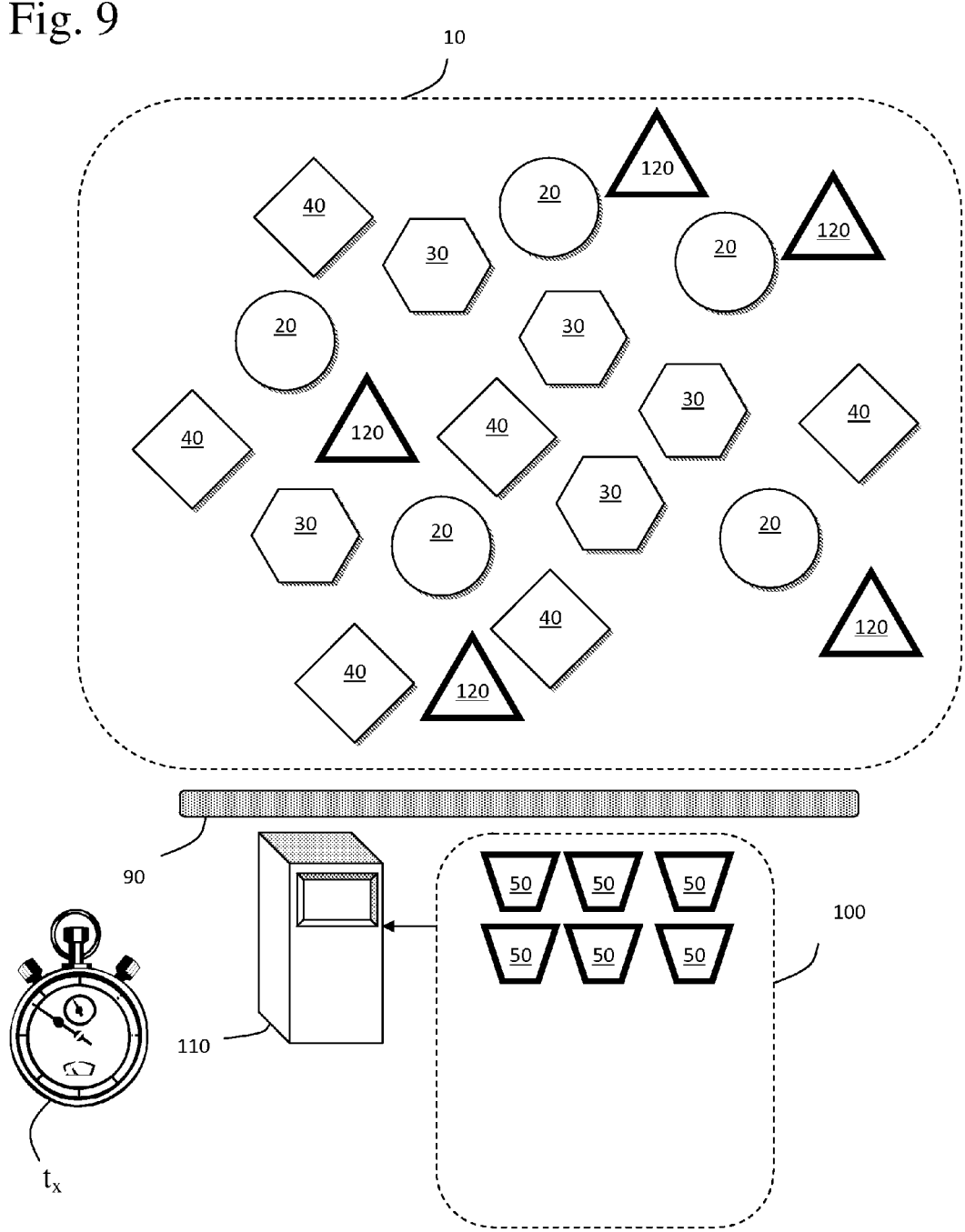
FIG. 9 is a diagrammatic view of a fluid sample showing a first type of proxy reporters have migrated across the selectively permeable membrane at a first time interval.
Figure 10:
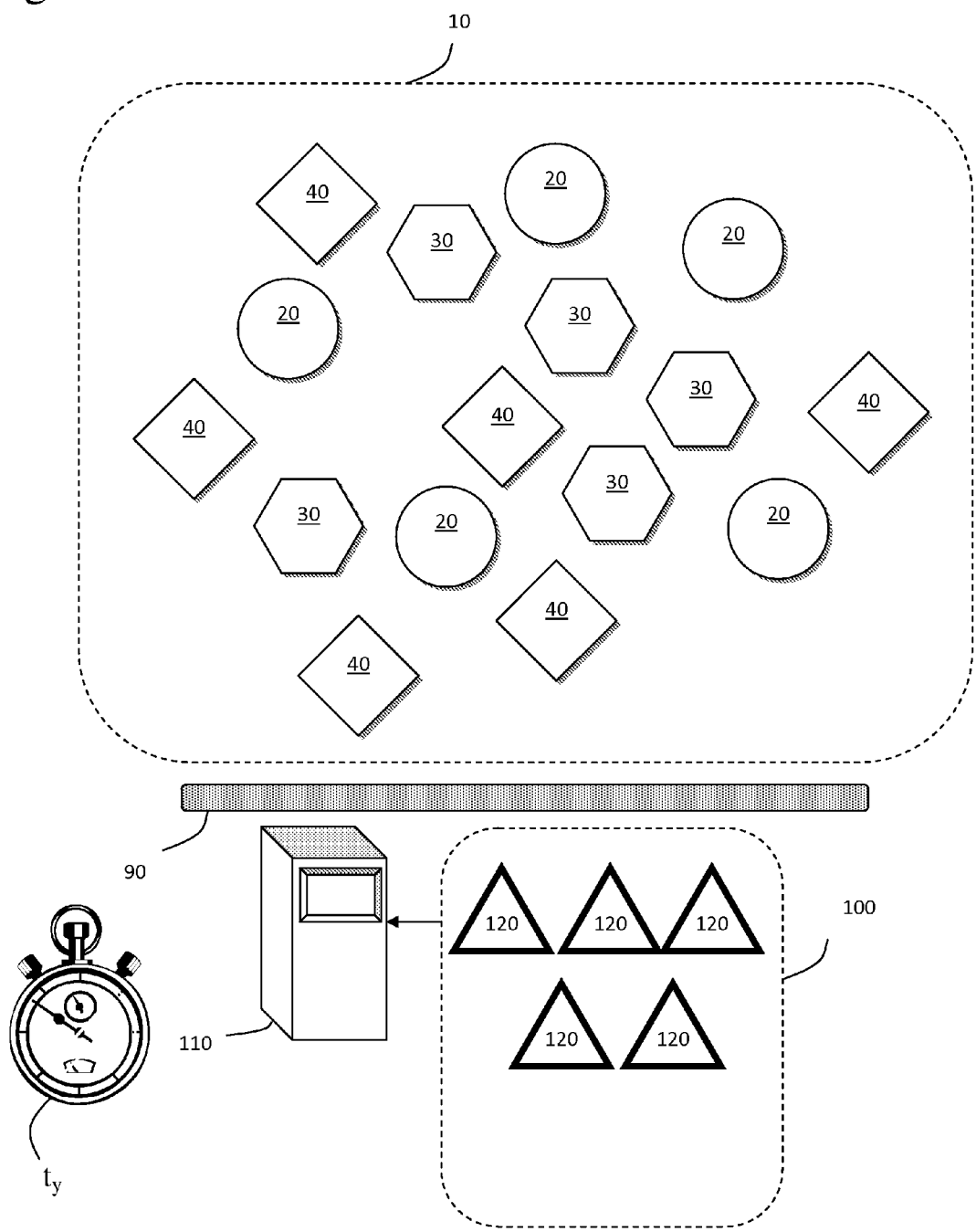
FIG. 10 is a diagrammatic view of a fluid sample showing a second type of proxy reporters have migrated across the selectively permeable membrane at a second time interval.

In FIG. 9, small massed proxy reporter 50 crosses from first phase 10 to second phase 100 across selectively permeable membrane during time interval x. Analytical detector 110 quantifies proxy reporter 50 resident in second phase 100 to provide a one-to-one correlation to molecule 40. In FIG. 10, larger massed proxy reporter 120 crosses from first phase 10 to second phase 100 across selectively permeable membrane during time interval y. The larger mass of proxy reporter 120 moves more slowly through selectively permeable membrane 90 providing a temporal analysis for analytical detector 110 to quantify the proxy reporter 120 resident in second phase 100. As noted in the previous example above, fluid sample in first phase 10 is returned to its original state.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting the concentration of a target molecule within a fluid sample, comprising the steps of:
   preselecting at least one tag that binds the target molecule;
   forming a molecule-tag complex by introducing the at least one tag to the fluid sample in a sufficient concentration to bind to all available target molecules in the fluid sample;
   extracting all unbound tags from the fluid sample;
   unbinding the tags from the molecule-tag complex;
   providing a membrane selectively permeable to the tags and impermeable to the target molecule;
   migrating the tags unbound from the molecule-tag complex across the membrane leaving the fluid sample substantially unaltered; and
   quantifying the tags unbound from the molecule-tag complex that migrated across the membrane.

2. The method of claim 1 wherein the quantification is performed by an analytical detector selected from the group consisting of optical detectors, electrochemical detectors and mass spectrometers.

3. The method of claim 1 wherein the unbinding step is effectuated by a method selected from the group consisting of photocleaving, chemical reaction, antibody recognition, molecular imprinted polymer reaction, oligonucleotide linkage and metal affinity reaction.

4. The method of claim 1 wherein the step of migration is performed by a method selected from the group consisting of charge, temperature and pressure gradient.

5. A method of detecting the concentration of a plurality of target molecules within a fluid sample, comprising the steps of:
   preselecting a first tag that binds to a first target molecule;
   preselecting a second tag that binds to a second target molecule;
   forming a first molecule-tag complex and a second molecule-tag complex by introducing the first and second tags to the fluid sample, in sufficient concentrations to saturate all available target molecules;
   extracting all unbound tags from the fluid sample;
   unbinding the first and second tags from the first and second molecule-tag complexes;
   providing a membrane selectively permeable to the first and second tags unbound from the first and second molecule-tag complexes whereby the first tag migrates through the membrane at a first rate and the second tag migrates through the membrane at a second rate;
   migrating the first and second tags unbound from the first and second molecule-tag complexes across the membrane; and
   quantifying the first and second tags unbound from the first and second molecule-tag complexes that migrated across the membrane on a temporal basis whereby the quantification correlates the first tags unbound from the first molecule-tag complex that migrated through the membrane at the first rate with the presence of the first target molecule in the sample and the second tags unbound from the second molecule-tag complex that migrated through the membrane at the second rate with the presence of the second target molecule in the sample.

6. The method of claim 5 wherein the quantification is performed by an analytical detector selected from the group consisting of optical detectors, electrochemical detectors and mass spectrometers.

7. The method of claim 5 wherein the unbinding step is effectuated by a method selected from the group consisting of photocleaving, chemical reaction, antibody recognition, molecular imprinted polymer reaction, oligonucleotide linkage and metal affinity reaction.

8. The method of claim 5 wherein the first and second tags are variable mass units, the first tag having a mass value quantitatively distinct from a mass value of the second tag.

9. The method of claim 5 wherein the step of migration is performed by a method selected from the group consisting of charge, temperature and pressure gradient.

* * * * *